United States Patent [19]

Lizardi et al.

[11] Patent Number: 4,615,973
[45] Date of Patent: Oct. 7, 1986

[54] **GENETICALLY ENGINEERED ORGANISMS EXPRESSING SURFACE PROTEINS OF *T. CRUZI***

[75] Inventors: Paul Lizardi, New York, N.Y.; Nadia Nogueira, Princeton, N.J.

[73] Assignee: The Rockefeller University, New York, N.Y.

[21] Appl. No.: 537,798

[22] Filed: Sep. 30, 1983

[51] Int. Cl.[4] .................... A61K 39/005; C12P 21/00; C12N 15/00; C12M 1/02

[52] U.S. Cl. .................................. 435/68; 435/172.3; 435/317; 935/12; 935/29; 935/38; 935/56; 935/65; 536/27; 424/88; 530/395

[58] Field of Search ...................... 435/68, 172.3, 258, 435/317, 947; 935/15, 29, 38, 56, 65, 73; 260/112 R, 112 B; 424/88; 536/27

[56] References Cited

U.S. PATENT DOCUMENTS 4,466,917 8/1984 Nussenzweig et al. ......... 260/112 R

FOREIGN PATENT DOCUMENTS 0044710 1/1982 European Pat. Off. ............ 435/172

OTHER PUBLICATIONS

Nogueira et al., *Proc. Natl. Acad. Sci.,* vol. 79(2), pp. 1259–1263, Feb. 1982, "Specific Glycoprotein Antigens on the Surface of Insect and Mammalian Stages of *Trypanosoma cruzi*".

Pawlowski et al., *J. Biol. Chem.,* vol. 250(6), pp. 325–375, "Identification and Purification of Collagen--Synthesizing Polysomes with Anti-Collagen Antibodies".

Hopp et al. *Proc. Nat. Acad. Sci.,* vol. 78(6), pp. 3824–3828, Jun. 1981, "Prediction of Protein Antigenic Determinants from Amino Acid Sequences".

Pays et al. *Chem. Abst.,* vol. 9Y, No. 99583t, 1981, "Cloning and Characterization of DNA Sequencer Complementary . . . of *Trypanosoma brucei*".

*Primary Examiner*—Blondel Hazel
*Assistant Examiner*—Robin Lyn Teskin
*Attorney, Agent, or Firm*—Felfe & Lynch

[57] ABSTRACT

Genetically engineered plasmids which express DNA encoding for insect stage specific glycoproteins of *Trypanosoma cruzi* are disclosed. The glycoproteins offer potential diagnostic utility for the detection of Chagus disease.

14 Claims, No Drawings

GENETICALLY ENGINEERED ORGANISMS EXPRESSING SURFACE PROTEINS OF *T. CRUZI*

This invention concerns genetically engineered organisms which express surface proteins of *T. cruzi*, the causative agent of Chagas disease. The proteins are immunogenic and are useful in detection of infection and immunoprophylaxis of the disease.

BACKGROUND

Two major surface antigens on *Trypanosoma cruzi* have been identified (Nogueira, N., Chaplan, S., Tydings, J., Unkeless, J. and Cohn, Z., J. Exp. Med. 153 629 (1981)). One, a Mr 75,000 glycoprotein (GP) is specific for the culture forms (insect - host stages) of the organisms - epimastigotes and metacyclic trypomastigotes. The other, a Mr 90,000 GP is specific for vertebrate - host stages of the organisms (bloodstream - form trypomastigotes). The two GP are unrelated and do not cross react immunogeneically. Because of their specificity, the surface proteins are potential diagnostic markers for Chagas disease.

SUMMARY

Recombinant plasmids harboring clones of double-stranded cDNA for coding an insect stage specific surface glycoprotein of *T. cruzi* have been constructed. The bacterial clones express the recombinant protein making it useful as a source of large amounts of antigen for both diagnostic and immunophrophylactic purposes.

DETAILS

Details on the isolation, and characterization of the Mr 75,000 and Mr 90,000 surface glycoproteins of *T. cruzi* have been disclosed in the publications by Nogueira et al. J. Exp. Med. 153 629 (1981) and Nogueira et al. Proc. Nat'l. Acad. Sci. USA 79 1259 (1982) which are hereby incorporated by reference.

Availability of Plasmid

The plasmids disclosed in the present invention bear the deposit number P1F8 and are deposited with The Rockefeller University, 1230 York Ave., New York, N.Y. 10021. Preferred plasmids of the present invention are also deposited at the American Type Culture Collection, Bethesda, Maryland and bear ATCC deposit number 40082.

Deposit is for the purpose of enabling disclosure only and is not intended to limit the concept of the present invention to the particular materials deposited.

PREPARATION OF PLASMIDS

Poly A+ RNA was isolated from 3 week-old strain epimastigote cultures, purified by oligo dT cellulose chromotography, and translated in vitro in the wheat germ cell-free translation system. Translation products were immunoprecipitated with either the IgG fraction of serum from a patient with chronic Chagas disease or with rabbit antiserum raised against epimastigote surface proteins. The IgG fraction of patients with Chagas' disease recognized 4 major bands of the in vitro translated material, one of which, a 34,000 Mr peptide may be the unglycosilated precursor of 75,000 Mr peptide.

The total polyA+ RNA was converted to cDNA with reverse transcriptase. The double-stranded cDNA was inserted into the Pst I site of the plasmid pUC13 by G-C tailing and the recombinant plasmids used to transform *E. coli* JM83. Colonies were selected for ampicillin resistance and initially screened by plating on YT medium supplemented with X-gal. Inserts into the cloning site disrupt the coding of B-galactosidase, resulting in the loss of complementation and enzymatic activity. Thus, plasmids with inserts gave rise to colonies that cannot hydrolyze X-gal and are consequently white. Plasmids without inserts or with small non-disruptive inserts gave rise to blue colonies. 1303 white, ampicillin-resistant colonies were selected for further screening by in situ radioimmunoassay.

Selection of Specific Plasmids

Bacterial cells were transferred to nitrocellulose filters, grown overnight, and lysed in situ. The filters were then incubated with the patient serum, washed extensively, and stained with $I^{125}$-labelled protein A from *S. aureus.* Eight colonies gave a strong positive signal upon re-screening with the patient serum. None of the eight, however, reacted with anti-75K monoclonal antibodies or with rabbit antiserum anti-75K.

Analysis of plasmid DNA from these eight clones showed inserts ranging in size from 100 base pairs to 600 base pairs. Thus, even short insert sequences can produce antigenic fragments recognized by polyvalent serum.

Because of its unusual culture morphology, one clone, p1F8, was chosen for further study. Unlike the other immunoreactive clones or its JM83 parent, p1F8 grows in liquid culture as a rough strain which suggests that the trypanosome polypeptide may be expressed on the bacterial cell surface.

p1F8 contains a pUC13 plasmid with a cDNA insert of 600 base pairs. To prove its trypanosome origin, the $^{32}P$-labelled insert was hybridized with trypanosome DNA in a Southern blot. The cloned DNA hybridized to several fragments generated by Hind II, Pst I, Sal I, or BamH I digestion of total DNA isolated form epimastigotes. These restriction enzymes do not cut the 600 basepair insert itself. This multiple banding pattern could result from the presence of intervening sequences or multiple gene copies.

The $^{32}P$-labelled insert was also used as the probe in a Northern blot of epimastigote RNA. The probe hybridized to an RNA of approximately 1000 nucleotides in both total RNA and polyA+ RNA preparations. It also hybridized to a second species of approximately 2100 nucleotides in the total RNA. In comparison, there is very little hybridization in a Northern blot of total RNA or polyA+ RNA isolated from vertebrate-stage parasites (tryptomastigotes). The 2100 nucleotide species is also present in the total tryptomastigote RNA. The results of these blot experiments strongly suggest stage-specific mRNA processing.

The difference in size between the 1000 nucleotide mRNA and the 600 base-pair cDNA insert indicates that the pIF8 clone must not code for a full-length gene. However, since the patient serum is able to react with the bacteria, the clone must encode and express at least one epitope. Nogueira has shown that all Chagas' disease patient sera tested recognize the same trypanosome antigens. Therefore, the p1F8 clone is likely to be useful in the diagnosis of the chronic illness.

Immunological Detection of Clones Containing T. cruzi cDNA Which Expresses Surface Proteins After lysis and washing, the filters were incubated for two hours at room temperature with the IgG fraction of Chagas disease patient serum diluted 1/300 into 50 mM tris-HCl/150 mM NaCL/3% BSA/1% NP-40/0.2% SDS. The serum had been pre-adsorbed with lysate prepared from the parental bacterial string JM83. The filters were then washed extensively with several changes of tris-saline and incubated for one hour at room temperature with $I^{125}$ labelled protein A (specific activity approximately $5\times10^6$ cpm/ug) diluted to $10^6$ cpm/ml in the same incubation buffer. The filters were washed extensively in the tris-saline buffer containing NP-40 and SDS. Protein A was labelled using the iodogen technique. Total epimastigote lysate served as a positive control on all filters. FIG. 2 illustrates the results.

This intraction between clone and lung antibodies against the surface protein of T. cruzi in human serum forms an essential basis for a diagnostic method for Chagas disease. These cloned peptides or their synthetic counterparts may be used in this method.

Northern Blot Analysis of RNA from Epimastigotes and Tryptomastigotes

The RNA samples were electrophoresed on a 1 M formaldehyde-1% agarose slab gel and blotted overnight onto BA83 nitrocellulose paper (Scheicher and Schuell). The filter paper was pre-hybridized for 4 hours at 42° C. in 50% formamide, 5XSSC, 4X Denhardt's buffer, 0.1% SDS, and 10% dextran sulfate. It was then hybridized for 12 hours in this same solution containing the $^{32}$P-labelled p1F8 probe and 100 ug/ml E. coli DNA. The filter was washed in 2xSSPE+0.1% SDS for 30 minutes at 37° C. and then in 0.1XSSPE+0.1% SDS at 37 C. for 30 minutes.

What is claimed:

1. Genetically engineered plasmids comprising DNA expressing insect stage specific surface glycoprotein of T. cruzi.
2. Plasmid of claim 1 wherein said surface glycoprotein is the Mr 75,000 T. Cruzi surface glycoprotein.
3. Plasmid of claim 1 wherein said DNA is isolated from T. cruzi.
4. Plasmid of claim 1 wherein said DNA is chemically synthesized.
5. Genetically engineered plasmid comprising DNA or RNA complementary to the DNA which expresses insect stage surface glycoprotein of T. cruzi.
6. Plasmid of claim 1 comprising pTC 1 F8.
7. DNA coding for insect-stage specific Mr 75,000 surface glycoprotein of T. cruzi.
8. DNA expressing T. cruzi insect stage specific surface glycoproteins wherein said DNA is incorporated in an appropriate plasmid and said plasmid is further incorporated in an appropriate microorganism.
9. DNA of claim 8 wherein said host/vector system is plasmid puC13 in E. coli K12.
10. DNA of claim 7 isolated from T. cruzi or chemically synthesized.
11. DNA or RNA complementary to DNA of claim 7.
12. DNA or RNA of claim 11 in a suitable bacterial host/vector system.
13. Method of producing insect stage specific surface glycoproteins of T. cruzi comprising culturing microorganisms containing plasmids which contain DNA expressing said glycoproteins, under conditions favoring expression of said glycoproteins and harvesting glycoproteins therefrom.
14. T. cruzi insect stage glycoproteins expressed by genetically engineered plasmid p TC 1 F8.

* * * * *